(12) United States Patent
Lochard et al.

(10) Patent No.: US 9,028,806 B2
(45) Date of Patent: May 12, 2015

(54) METHOD FOR IMPREGNATION WITH SUPERCRITICAL $CO_2$

(75) Inventors: Hubert Lochard, Brens (FR); Bernard Freiss, Castres (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 166 days.

(21) Appl. No.: 13/320,453

(22) PCT Filed: May 12, 2010

(86) PCT No.: PCT/EP2010/056582
§ 371 (c)(1),
(2), (4) Date: Nov. 14, 2011

(87) PCT Pub. No.: WO2010/130799
PCT Pub. Date: Nov. 18, 2010

(65) Prior Publication Data
US 2012/0064130 A1 Mar. 15, 2012

(30) Foreign Application Priority Data
May 15, 2009 (FR) ..................... 09 53221

(51) Int. Cl.
*A61K 8/73* (2006.01)
*A61K 47/00* (2006.01)
*A61K 9/16* (2006.01)

(52) U.S. Cl.
CPC ............. *A61K 9/1694* (2013.01); *A61K 9/1635* (2013.01); *A61K 9/1652* (2013.01)

(58) Field of Classification Search
USPC .......................... 514/16.6, 781; 424/494, 409
See application file for complete search history.

(56) References Cited

FOREIGN PATENT DOCUMENTS

| EP | 1 894 565 A1 | 3/2008 |
|---|---|---|
| WO | WO 94/18264 A1 | 8/1994 |
| WO | WO 98/08495 A1 | 3/1998 |
| WO | WO 99/25322 A2 | 5/1999 |

OTHER PUBLICATIONS

Gong et al, J. Pharm & Biomed. Analysis, 2008, 48(4), 1112-1119.*
Albertini et al., "Evaluation of β-lactose, PVP K12 and PVP K90 as excipients to prepare piroxicam granules using two wet granulation techniques", European Journal of Pharmaceutics and Biopharmaceutics, vol. 56 (2003) pp. 479-487.
Cortesi et al., "Supercritical fluids chromatography for impregnation optimization", Journal of Supercritical Fluids, vol. 19 (2000) pp. 61-68.
Gong et al., "Characterization and drug release investigation of amorphous drug-hydroxypropyl methylcellulose composites made via supercritical carbon dioxide assisted impregnation", Journal of Pharmaceutical and Biomedical Analysis, vol. 48 (2008) pp. 1112-1119.
International Search Report issued in PCT/EP2010/056582 on Mar. 25, 2011.
Manna et al., "Impregnation of PVP microparticles with ketoprofen in the presence of supercritical CO2", Journal of Supercritical Fluids, vol. 42 (2007) pp. 378-384.
Pasquali et al., "Supercritical fluid technologies: An innovative approach for manipulating the solid-state of pharmaceuticals", Advanced Drug Delivery Reviews, vol. 60 (2008) pp. 399-410.
Search report issued in French Application No. 722816 on Nov. 6, 2009.
Ugaonkar et al., "Effect on n-scCO2 on crystalline to amorphous conversion of carbamazepine", International Journal of Pharmaceutics, vol. 333 (2007) pp. 152-161.

* cited by examiner

*Primary Examiner* — Misook Yu
*Assistant Examiner* — Kauser M Akhoon
(74) *Attorney, Agent, or Firm* — Birch, Stewart, Kolasch & Birch, LLP

(57) ABSTRACT

The present invention relates to a batch method for impregnating a nonporous polymer pharmaceutical carrier with an active substance, characterized in that said method includes the following consecutive steps: a) mixing the active substance and the nonporous polymer pharmaceutical carrier, the pharmaceutical carrier being in a solid form and insoluble in supercritical $CO_2$ and not being non-crosslinked polyvinylpyrrolidone; b) performing a step of molecular diffusion in the absence of water by contacting, in a static mode without agitation, the mixture obtained in step a) with supercritical $CO_2$ at a pressure of 80 to 170 bars, at a temperature of 31 to 90° C. for 1 to 6 hours; c) recovering the polymer pharmaceutical carrier impregnated with the active substance obtained in step b), the impregnated pharmaceutical carrier being nonporous and being in a solid form and the active substance being in an amorphous form, the method being implemented in the absence of an additional solvent. The invention further relates to a polymer pharmaceutical carrier in a nonporous solid form impregnated with an active substance characterized in that said carrier can be obtained by the method according to the present invention, in that the active substance is in an amorphous form and is water-soluble, and in that the polymer pharmaceutical carrier is not non-crosslinked polyvinylpyrrolidone and is insoluble in supercritical $CO_2$.

13 Claims, No Drawings

METHOD FOR IMPREGNATION WITH SUPERCRITICAL $CO_2$

The present invention relates to a method for impregnating a polymeric pharmaceutical carrier with an active substance using supercritical $CO_2$.

Impregnation methods using supercritical $CO_2$ have already been described in the prior art. However, none of the prior art describes a quick, easy-to-implement method, suitable for use regardless of the type of polymeric carrier and, in particular, a polymeric carrier more commonly known as a disintegrating agent than as a binder, and suitable for use with any type of active substance, regardless of whether it is soluble in aqueous media.

In this way, the article by Manna et al (The Journal of Supercritical Fluids, Volume 42, Issue 3, October 2007, pages 378-384) describes a continuous method for impregnating polyvinylpyrrolidone (PVP) with ketoprofen. However, the PVP used is not cross-linked. Non-cross-linked PVP is a well known binding agent for obtaining stabilised amorphous forms, regardless of the impregnation method used. Moreover, the method described is very slow since it is associated with the solubility of the active substance in $CO_2$ (one test=5 days). It is thus not suitable for use with active substances that are insoluble in supercritical $CO_2$, unlike the method according to the present invention. Moreover, in this method, there is no prior mixing between ketoprofen and PVP since, on the contrary, the prior mixing is the one between the active substance and supercritical $CO_2$. The article by Ugaonkar et al (International. Needham Journal of Pharmaceutics, Volume 333, Issues 1-2, 21 Mar. 2007, pages 152-161) describes the effect of n-$scCO_2$ on the conversion of carbamazepine from the crystalline form thereof to the amorphous form thereof. However, the method described does not use supercritical $CO_2$ but liquid $CO_2$ (P=63 bar, T=25° C.) referred to as near supercritical $CO_2$. Moreover, before each test, the authors carried out "pre-drying" of the polymer at 80° C. for 16 hrs which prolongs the method. Based on the DRX results given in table 1, significant, but partial, amorphisation is only obtained with low molecular weight PVP, i.e. non-cross-linked PVP. These results are confirmed by DSC wherein the attenuation is very limited. The very significant analytical variability observed in the results described in this article is explained by very significant differences in particle size between the large polymer particles and the active substance. The differences in dissolution obtained are insignificant and attributable to the presence of the carrier (no difference between treated vs. Untreated). The authors do not prove that partially amorphous forms are stabilised. The authors conclude that the $CO_2$/polymer interaction enables amorphisation (page 160) and the polymer chain flexibility is of major importance. In this way, the authors thus state that only polymers having a satisfactory chain flexibility (such as non-cross-linked PVP) make it possible to obtain amorphisation of the active substance during the impregnation thereof in the carrier. In this way, according to the authors, it is thus not possible to use the method described in this article with any carrier and particularly with polymers wherein the chains are relatively rigid such as cross-linked PVP.

The article by Banchero et al (The Journal of Supercritical Fluids, In Press, Corrected Proof, Available online 30 Jan. 2009) describes a method for impregnating PVP with piroxicam using a supercritical solvent. However, the method described is particularly slow: between 20-48 hrs. Moreover, the pressure used is very high: approximately 300 bar. The same applies to the operating temperature: approximately 100° C. Finally, the PVP used is non-cross-linked PVP, a well known binding agent for obtaining stabilised amorphous forms of active substance, regardless of the impregnation method used.

The article by Albertini et al (European Journal of Pharmaceutics and Biopharmaceutics 56 (2003) p 479-487) describes a method for amorphising piroxicam by means of mere granulation with water vapour (60° C., in a vacuum) using b-lactose, PVP K12 and PVP K90 as carriers. This results in amorphisation stabilised over 1 year (moreover on p. 387, the authors specify that non-cross-linked PVP is well known as an inhibitor of active substance crystallisation).

The article by Gong et al (Journal of Pharmaceutical and Biomedical Analysis, Volume 48, Issue 4, 1 Dec. 2008, pages 1112-1119) describes a method for impregnating hydroxypropyl methylcellulose with indometacin using supercritical $CO_2$. However, the method is performed with stirring during the step using supercritical $CO_2$ (180 rpm): this renders the method economically non-viable due to the very high extra cost since a pressurised stirring system is required. Furthermore, the autoclave should only be filled partially to enable mixing of the supercritical $CO_2$ around the powder (the financial cost of direct powder mixing in a pressurised chamber is prohibitive). Moreover, with the method described, only tests at very high temperatures: 110° C. and 130° C. made it possible to obtain amorphisation (these temperatures are very similar to the melting point of the active substance (160° C.)).

The inventors unexpectedly discovered a simple and easy novel method, not having the drawbacks of the prior art, and in particular suitable for use regardless of the type of polymeric pharmaceutical carrier, in particular with carriers which are not known as active substance crystallisation inhibitors, regardless of the type of active substances, for example with active substances soluble in an aqueous medium, for obtaining impregnation of a pharmaceutical polymeric carrier with an active substance, the active substance thus being in a stabilised amorphous form. Such a method comprises a static mode molecular diffusion step using supercritical $CO_2$.

Methods using such a step have already been described in the prior art. However, they have never been used without stirring for impregnating a polymeric pharmaceutical carrier according to the invention, and in particular a non-porous carrier, without adding a solvent other than supercritical $CO_2$.

In this way, patent application WO03/043604 describes a method for including an active substance in a porous substrate comprising a static mode molecular diffusion step. However, such a method makes it possible to obtain a complex (or inclusion compound) between the active substance and the porous substrate and not obtain a polymeric carrier impregnated with the active substance. Moreover, the substrate used is porous and is not a polymeric carrier since it is cyclodextrin. Furthermore, the method is only used with very specific active substances, i.e. an active substance that is slightly soluble in an aqueous medium, the porous substrate being soluble. Moreover, the method is relatively slow since the molecular diffusion step lasts at least 16 hours. Finally, this method necessarily comprises a washing step with supercritical $CO_2$ of the complex obtained, which prolongs the method further.

Patent application WO20047/096284 describes a method for preparing soluble molecular complexes comprising a static mode molecular diffusion step. However, such a method makes it possible to obtain a complex between the active substance and the host molecule and not obtain a polymeric carrier impregnated with the active substance. Indeed, complexing is the inclusion of an invited molecule (in this case the active substance) in the cavity of a host molecule. It is determined by a complexing equilibrium defined by a constant Ks. The host molecule thus necessarily has a cavity and is thus porous, which is not the case of the polymeric pharmaceutical carrier according to the invention. Moreover, the host molecule is not a polymeric carrier since it is cyclodextrin. Moreover, the method necessarily comprises the presence of a solvent other than supercritical $CO_2$ referred to as the diffusion agent such as water for example. As shown in the examples, the absence of this agent prevents the formation of molecular complexes. Therefore, it does not make it possible to obtain a dry powder directly after the molecular diffusion step, unlike the method according to the invention. Furthermore, the method is only used with very specific active substances, i.e. an active substance that is slightly soluble in an aqueous medium, the host molecule being soluble.

U.S. Pat. No. 6,414,050 describes a method for preparing a composition by contacting, using supercritical $CO_2$, a polymer substrate and a biofunctional material substrate. However, the pressure and temperature conditions selected for this contacting are such that they make it possible to reduce the viscosity of the polymer so as to plasticise same (i.e. softening occurs) or melt and/or swell same. The conditions are thus relatively severe and there is a visible modification of the polymer structure to the naked eye. Moreover, the composition obtained is porous since, due to the liquefaction of the polymer, when the $CO_2$ is removed, bubbles are formed in the polymer which is in the process of solidifying. Furthermore, in all the examples, the contacting step was performed with stirring, which poses problems for industrialising the method due to the extra costs incurred. Moreover, there is no change of the physical form of the active substance, i.e. there is no amorphisation of this active substance with the method described. Furthermore, there is no prior mixing between the active substance and the polymer since the contacting step with supercritical $CO_2$ takes place under stirring. Finally, to obtain a powder, it is necessary to spray the product obtained via a spraying nozzle which complicates the method.

The patent application WO 94/18264 describes the impregnation of a polymer with an active substance using supercritical $CO_2$. However, to carry out this impregnation, a liquid is added to the mixture, this liquid possibly being water, in particular, and is in general a solubilising agent of the active substance. Moreover, in the examples, the active substance is in solution (examples 24-26, page 46, 127) and not solid. Furthermore, in examples 2 and 4 of the table produced with no presence of water, and thus without adding liquid, and either in two separate flasks, or in the same flask, at 60 degrees and 13.8 MPa, there is no impregnation of the beads which remain white.

Therefore, the method appears not to be suitable for implementation, according to the document, in the absence of liquid and in particular in the absence of water.

However, the presence of a liquid involves the drawback of requiring the removal thereof at the end of the impregnation method.

The application WO 99/25322 discloses the impregnation of cross-linked polyvinyl pyrrolidone or cross-linked sodium glycolate starch with active substances such as ketoprofen using supercritical $CO_2$ by means of a continuous method.

The active substance is first solubilised in the supercritical fluid before being added to the polymer. The problem of this type of method is that it is only suitable for use for active substances soluble in supercritical $CO_2$.

Moreover, although the static mode is disclosed in document D2, only the dynamic mode is found in the examples.

On the basis of the data described in this application, it is easy to access the quantity of $CO_2$ required to process 1 kg. In example 1, the author impregnates 1.225 g of Nimesulide in 5 g of cross-linked PVP. For this, 43 kg of $CO_2$ (for a liquid $CO_2$ density=approximately 0.9 kg/liter), i.e. 35 tonnes of $CO_2$/kg of Active substance, is used.

In example 2, the author impregnates 1.06 g of aciclovir in 5 g of cross-linked methacrylate. For this, 130 kg of $CO_2$ (for a liquid $CO_2$ density=approximately 0.9 kg/liter), i.e. 122 tonnes of $CO_2$/kg of Active substance, is used.

According to the article by A. Bounaceur et al./(J. of Supercritical Fluids 41 (2007) 429-439), the molar fraction of Ketoprofen in pure $CO_2$ is approximately $y=4.1\times10-5$ (200 bar, 65° C.). Therefore, in order to impregnate Ketoprofen based on this document, it is necessary to use at least 4.3 tonnes of $CO_2$/kg of Active substance.

The $CO_2$ content to be used is thus too high to be able to industrialise this process which thus has a prohibitive $CO_2$ cost.

Therefore, the inventors discovered a method combining the advantages of the use of a static mode molecular diffusion step with supercritical $CO_2$, without the disadvantages of the prior art, such as for example:

the need to use a porous carrier or an excessively long method for example due to an excessive number of steps (additional washing with supercritical $CO_2$ or spraying with a nozzle), or excessively severe temperature and pressure conditions inducing the liquefaction or at least the softening of the polymer or prolonging the method or the use of stirring during the molecular diffusion step, the use of an excessive quantity of $CO_2$ or the mandatory presence of another fluid in addition to $CO_2$.

Therefore, the present invention relates to a batch method for impregnating a polymeric pharmaceutical carrier with an active substance, characterised in that it comprises the following consecutive steps:

a) mixing the active substance and the non-porous polymeric pharmaceutical carrier, the pharmaceutical carrier being in solid form and insoluble in supercritical $CO_2$ and not being non-cross-linked polyvinylpyrrolidone;

b) performing a molecular diffusion step in the absence of water by contacting, in static mode without stirring, the mixture obtained in step a) with supercritical $CO_2$ at a pressure between 80 and 170 bar and at a temperature between 31 and 90° C. for between 1 and 6 hours, c) recovering the polymeric pharmaceutical carrier impregnated with the active substance obtained in step b), the impregnated pharmaceutical carrier being non-porous and being in solid form and the active substance being in amorphous form, the method being implemented in the absence of an additional solvent.

Using the method according to the present invention, the quantity of $CO_2$ required to process 1 kg of AS is only dependent on the bulk density of the powder and the impregnated active substance content.

In this way, on the basis of the following assumptions:

Bulk density of powder=500 g/liter

Impregnated active substance content=20%

Only 10 kg of $CO_2$/kg of Active substance should be used.

In this way, this method can be performed using 400 times less $CO_2$ for ketoprofen and 12,000 times less $CO_2$ for aciclovir than in the method described in patent application WO 99/25322. This reduces the "solvent" cost accordingly and hugely reduces the investments required.

Within the scope of the present invention, the polymeric pharmaceutical carrier used is non-porous. Therefore, it is not a cyclodextrin or a host molecule shaped like a cage and enabling the formation of a molecular complex. Indeed, the product obtained with the method according to the present invention is not a complex between the carrier and the active substance but a carrier impregnated with the active substance. The product obtained is thus a solid dispersion on a molecular level between the polymeric pharmaceutical carrier and the active substance and not an insertion of the active substance in the cavity of a porous carrier. In this way, the active substance impregnating the polymeric carrier is in amorphous form. Therefore, in particular, a physical modification of the active substance takes place during the impregnation thereof.

According to the present invention, the term "polymeric carrier" refers to any polymeric carrier having a long chain. Therefore, it is not an oligomer such as a cyclodextrin or lactose. In particular, the polymeric chain of the polymeric carrier according to the invention comprises at least 10 units for example at least 20 units.

According to the present invention, the term "pharmaceutical carrier" refers to any carrier suitable for use in a pharmaceutical, nutritional or veterinary medium. In particular, it may consist of a carrier acting as a diluting, binding, coating, anti-adherent, disintegrating, plasticising, solubilising, lubricating, stabilising, anti-caking, anti-moisture, taste masking or filler, release profile modification (sustained release for example) agent, etc.

In one particular embodiment, it consists of a cellulose polymer, such as for example, cellulose, microcrystalline cellulose, hypromellose, particularly acetate succinate, methyl cellulose, ethyl cellulose, hydroxypropyl cellulose, hydroxypropyl methyl cellulose, or carboxymethyl cellulose, a wax, a plant-based or synthetic gum, such as guar gum, gum arabic, xanthan or carob bean gum, a polyethylene glycol, a phthalic polymer such as cellulose aceto-phthalate, cross-linked polyvinylpyrrolidone, starch or a maltodextrin or a mixture thereof. In particular, it does not consist of a polysaccharide and/or a polyose. In a further particular embodiment, the polymeric pharmaceutical carrier is selected in the group consisting of a cellulose polymer, cross-linked polyvinylpyrrolidone and the mixture thereof, in particular in the group consisting of carboxymethyl cellulose, of sodium for example, hydroxypropyl methyl cellulose, methyl cellulose, cross-linked polyvinylpyrrolidone and the mixture thereof.

The polymeric pharmaceutical carrier according to the invention is in solid form at ambient temperature and thus during step a) of the method according to the invention. Moreover, the vitreous transition (Tg) and melting (Tf) point thereof is such that, during step b), the polymeric carrier remains in solid form and thus is not liquefied. Therefore, no swelling or plasticisation of the polymeric carrier occurs during this step. However, there is an increase in polymer chain mobility during step b), enabling the penetration of the active substance in the polymeric carrier and thus the impregnation thereof with the active substance.

The polymeric carrier according to the invention is not non-cross-linked polyvinylpyrrolidone. Indeed, such a carrier is already well known as an active substance crystallisation inhibitor and thus does not need to be impregnated using the method according to the present invention. Moreover, the mobility of the polymer chains thereof is particularly important. The method according to the present invention relates more to polymeric pharmaceutical carriers wherein the polymer chains are relatively immobile particularly at ambient temperature such as cross-linked PVP.

The polymeric pharmaceutical carrier suitable for use in the method according to the present invention is particularly insoluble in an aqueous medium.

Unexpectedly, the inventors observed that the method according to the present invention makes it possible to overexpress the functionalities of the polymeric pharmaceutical carrier used. Indeed, if a carrier is for example a disintegrating agent (such as cross-linked polyvinylpyrrolidone or sodium carboxymethyl cellulose), following the impregnation thereof with the active substance using the method according to the present invention, the disintegration power thereof is considerably enhanced (i.e. almost double). Moreover, it is very surprising to be able to impregnate a pharmaceutical polymeric carrier acting as a disintegrating agent with an active substance and obtain a stabilised amorphous form of the active substance.

The term "active substance", according to the present invention, refers to any active substance whether it is soluble or slightly soluble in an aqueous medium. This method is thus not limited to active substances which are slightly soluble in an aqueous medium. The purpose of impregnation is thus not only to enhance the dissolution of the active substance in the aqueous medium, but essentially to make it possible to obtain a stabilised amorphous form of the active substance. In this way, in particular, an active substance, wherein the amorphous form is not stabilised, will be used. In one particular embodiment, during step a), the active substance is in crystalline form. Moreover, during step c), the active substance is in amorphous form. Therefore, amorphisation of the active substance takes place during step b), i.e. during the impregnation of the polymeric pharmaceutical carrier with the substance. The active substance may be a pharmaceutical (examples include analgesics, antipyretics, aspirin and derivatives thereof, antibiotics, anti-inflammatories, anti-ulcer agents, antihypertensives, neuroleptics, antidepressants, oligonucleotides having a therapeutic activity, peptides having a therapeutic activity and proteins having a therapeutic activity), cosmetic or nutraceutical ingredient or a mixture thereof. In particular, the active substance is insoluble in supercritical $CO_2$ (such as vinflunine).

The term "active substance slightly soluble in an aqueous medium" refers, according to the present invention, to any active substance that is slightly soluble or insoluble in an aqueous medium and particularly having a solubility less than at least 20 µg/ml.

In particular, the active substance according to the invention is selected in the group consisting of anilide derivatives, epipodophyllotoxin derivatives, minoxidil, piroxicam, valeric acid, octanoic acid, lauric acid, stearic acid, tiaprofenic acid, opeprazole, econazole, miconazole, ketoconazole, astemizole, cyclobenziprine, nimesulide, ibuprofen, tefenadine, domperidone, naproxen, eflucimibe, ketoprofen, vinflunine, milnacipran, fenofibrate, iron sulphate monohydrate, iron sulphate heptahydrate and the mixture thereof, more specifically selected in the group consisting of ketoprofen, vinflunine, milnacipran, fenofibrate, iron sulphate monohydrate, iron sulphate heptahydrate and the mixture thereof.

The method according to the present invention is particularly advantageous for the impregnation:
  of ketoprofen in the carrier selected from: methyl cellulose, cross-linked PVP, HPMC and carboxymethyl cellulose,
  vinflunine in carboxymethyl cellulose,
  minalcipran in HPMC or methyl cellulose The term "supercritical $CO_2$" refers, according to the present invention, to $CO_2$ used at a temperature and a pressure greater than the critical value thereof.

The term "static mode" refers, according to the present invention, to a reaction or a method wherein all the reagents are simultaneously present and the reaction is allowed to take place. For example, in step b) of the present invention, the mixture obtained in step b) and supercritical $CO_2$ are placed in an autoclave and the reaction is left for a number of hours. The product mass does not change during the reaction. Conversely, in dynamic mode, the reagents are added as the reaction or production develops. Fluid circulation or stirring frequently occurs in the case of dynamic mode. The product mass changes during production.

Moreover, the method according to the invention is a batch method. In this way, all the ingredients required for the impregnation are added in one go at the start of step b) and the impregnated polymeric carrier is obtained at the end of step b).

No other ingredient is added or removed between the start and the end of step b).

In one particular embodiment, the mass ratio between the active substance and the polymeric pharmaceutical carrier in the impregnated polymeric pharmaceutical carrier is between 1 and 60%, in particular between 1 and 50%, more specifically between 20 and 35%, for example between 10 and 35%.

Step a) of the method according to the present invention is very important since it enables intimate mixing of both ingredients (polymeric pharmaceutical carrier+active substance) before the molecular diffusion step, which is performed without stirring. The term "intimate mixture" of A and B refers to a mixture of A and B wherein A and B are uniformly distributed within the mixture obtained. Step a) thus makes it possible to reduce the duration of step b). In particular, this step is performed with a mixer such as drum mixer, convective mixer, fluidised mixer or static mixer.

Particularly, the active substance during step a) is in solid form, more specifically in powder form, for example in crystalline form. In one particular embodiment during step a), the active substance and the polymeric pharmaceutical carrier are in solid form, in particular in powder form. The mixture obtained at the end of step a) is thus for example a physical mixture, particularly a dry powder.

Particularly, step a) is performed at ambient temperature and pressure.

Step b) of the method according to the present invention enables the impregnation of the polymeric pharmaceutical carrier. The use of supercritical $CO_2$ avoids the use of an organic solvent which subsequently needs to be removed from the impregnated polymeric pharmaceutical carrier obtained.

In one particular embodiment, step b) is performed in a closed reactor, particularly an autoclave. The mixture obtained in step a) is thus introduced into this reactors, concomitantly or consecutively with the $CO_2$. The $CO_2$ is introduced in gas form. The reactor is then closed and pressurised and brought to the desired temperature for the time required for the $CO_2$ to be in supercritical form and to obtain the impregnation of the polymeric pharmaceutical carrier with the active substance, without liquefaction or softening of said carrier. Indeed, throughout step b), the polymeric pharmaceutical carrier remains in solid form and in particular in powder form. There is no visible modification to the naked eye of the structure of the polymeric pharmaceutical carrier. Particularly, if the active substance is in solid form and in particular in powder form, the active substance also remains in solid form and in particular in powder form throughout step b) and there is visible modification to the naked eye of the structure of the active substance.

In one particular embodiment, the temperature in step b) is between 40 and 85° C., such as for example between 50 and 80° C.

In a further particular embodiment, the pressure in step b) is between 100 and 160 bar, for example equal to 150 bar.

In a further particular embodiment, there is no washing step with supercritical $CO_2$ after step b) and/or drying step and/or spraying step, in particular using a nozzle.

In one particular embodiment, the contact time in step b) is between 1 and 3 hours, for example equal to two hours.

Step b) of the method according to the present invention is performed without stirring, rendering the method easy to industrialise. Indeed, in view of the pharmaceutical carriers used within the scope of the present invention, and in particular in that the carrier retains the solid form thereof throughout step b), the use of stirring in a high pressure reactor is only possible on a laboratory scale (use of a reactor of a few liters) and not on an industrial scale. Indeed, to transmit the movement of the motor (which is at atmospheric pressure) to a stirring shaft (which is at high pressure), tightness cannot be provided with "conventional" seals. Therefore, a magnetic drive is used: a magnet driving another magnet, which limits the possibilities in terms of the stirring torque.

Within the scope of the present invention, the method is performed in the absence of an additional solvent. Water is particularly absent from step b) according to the present invention. The mixture obtained in step a) is dry. Similarly, the product obtained at the end of step b) is dry.

In this way, the only solvent present during step b) of the present invention is supercritical $CO_2$.

Advantageously, the method according to the present invention is performed in the absence of any other fluid, for example, liquid, for example water, other than supercritical $CO_2$.

In this way, in one particular embodiment of the invention, the only ingredients present are: the active substance, the pharmaceutical carrier and supercritical $CO_2$, particularly during step b).

Step c) makes it possible to recover and isolate the impregnated polymeric pharmaceutical carrier obtained following step b) and optionally separate same from the active substance which has not impregnated the polymeric carrier and/or the polymeric pharmaceutical carrier which has not been impregnated. For this, the reactor used in step b) is depressurised and cooled. $CO_2$ is removed in gas form.

The impregnated polymeric pharmaceutical carrier is in solid form.

If the polymeric pharmaceutical carrier was in powder form at the start of step b), then it remains in powder form after the impregnation thereof, i.e. at the end of step b) and during step c). In particular, due to the absence of water during step b) of the method according to the present invention, the powder obtained is a dry powder. Therefore, it is not necessary to dry this powder.

The active substance impregnating the polymeric pharmaceutical carrier is in stabilised amorphous form. In this way, this active substance retains the amorphous form thereof throughout the shelf-life thereof and in particular for at least 2 months, in particular for up to one year. The term "active substance in stabilised amorphous form" refers, according to the present invention, to any active substance having a tendency to crystallise or recrystallise kept in amorphous form for a longer period than if it was not processed with the method according to the present invention, in particular for a period of at least 6 months, more specifically for a period of at least 1 year.

The pharmaceutical carrier impregnated with the active substance can be used in the preparation of any pharmaceutical, cosmetic or nutraceutical composition wherein the presence of the active substance in amorphous form is required.

In particular, it can be used in the production of pills, tablets or capsules intended for oral administration.

The method according to the present invention is particularly advantageous for potentiating the functionality of the pharmaceutical carrier. In this way, it is possible, using a suitable pharmaceutical carrier, to obtain an active substance with delayed release for an active substance that is very soluble in water or to render an active substance that is slightly soluble in water soluble.

The present invention further relates to a polymeric pharmaceutical carrier in non-porous solid form impregnated with an active substance characterised in that it is obtainable with the method according to the present invention as described above, in that the active substance is in amorphous form and is soluble in water and in that the polymeric pharmaceutical carrier is not non-cross-linked polyvinylpyrrolidone and is insoluble in supercritical $CO_2$.

In one particular embodiment of the invention, the active substance is milnacipran, in particular in hydrochloride form, for example the (1S, 2R) enantiomer.

In a further particular embodiment, the polymeric pharmaceutical carrier is a filler agent, in particular selected from methyl cellulose, hydroxypropyl methyl cellulose and the mixtures thereof.

The present invention further relates to the polymeric pharmaceutical carrier in solid form impregnated with milnacipran according to the present invention for use as a medicinal product.

Finally, it relates to the polymeric pharmaceutical carrier in solid form impregnated with milnacipran, in particular in the (1S, 2R) enantiomer form, according to the present invention for use as a medicinal product having an antidepressant action and/or intended for treating depression, such as deep depression, resistant depression, psychotic depression, depression induced by interferon treatments, states of depression, manic depression syndrome, seasonal states of depression, episodes of depression linked with general health and depression due to mood-altering substances, bipolar disorders, schizophrenia, general anxiety, morosis and marasmus, stress-related disorders, panic attacks, phobias, post-traumatic disorders, social phobia, obsessive-compulsive disorders, behavioural disorders, drug addiction detoxification, immune system depression, fatigue and associated pain syndromes, chronic fatigue syndrome, autism, hyperactive attention disorders, sleep disorders, premenstrual dysphoric disorders, cardiovascular diseases, neurodegenerative diseases and anxiety and associated depression syndromes (Alzheimer's disease, Huntington's chorea, Parkinson's disease), urinary incontinence, eating disorders, bulimia nervosa, anorexia nervosa, obesity, apathy, migraine and/or irritable bowel syndrome and/or intended for treating fibromyalgia syndrome and/or other functional disorders, and/or for treating psychiatric disorders, particularly central nervous system disorders, more specifically while reducing the risk of suicidal tendencies.

The following examples are given for indicative and not limitative purposes.

EXAMPLES

Example 1

With Ketoprofen

Ketoprofen/Cross-Linked PVP (Polyvinylpyrrolidone)

Powder mixture: 1 g of Ketoprofen in crystalline form (SIGMA)+2 g of Polyplasdone XL 10 (ISP) manually with a mortar (step a) of the method according to the present invention).

Treatment with supercritical $CO_2$ (SC) at 150 bar, 80° C., 2 hrs (step b) of the method according to the present invention) by pressurising a controlled-temperature high-pressure autoclave containing the mixture.

Recovery of the powder (step c) of the method according to the present invention) by depressurising the autoclave.

1b Ketoprofen/Methyl Cellulose

Powder mixture: 1 g of Ketoprofen in crystalline form (SIGMA)+2 g of Metolose SM 4 (SEPPIC) manually with a mortar (step a) of the method according to the present invention).

Treatment with SC $CO_2$ at 150 bar, 80° C., 2 hrs (step b) of the method according to the present invention) by pressurising a controlled-temperature high-pressure autoclave containing the mixture.

Recovery of the powder (step c) of the method according to the present invention) by depressurising the autoclave.

1c Ketoprofen/Hydroxypropyl Methyl Cellulose (HPMC)

Powder mixture: 1 g of Ketoprofen in crystalline form (SIGMA)+2 g of Benecel MP 843 HPMC (ASHLAND) manually with a mortar (step a) of the method according to the present invention).

Treatment with SC $CO_2$ at 150 bar, 80° C., 2 hrs (step b) of the method according to the present invention) by pressurising a controlled-temperature high-pressure autoclave containing the mixture.

Recovery of the powder (step c) of the method according to the present invention) by depressurising the autoclave.

1d (Comparative Example) Ketoprofen/Lactose

Powder mixture: 1 g of Ketoprofen in crystalline form (SIGMA)+2 g of lactose manually with a mortar (step a) of the method according to the present invention).

Treatment with SC $CO_2$ at 150 bar, 80° C., 2 hrs (step b) of the method according to the present invention) by pressurising a controlled-temperature high-pressure autoclave containing the mixture.

Recovery of the powder (step c) of the method according to the present invention) by depressurising the autoclave.

Analytical Protocol and Results Relating to Amorphisation of the Active Substance (Ketoprofen):

Differential scanning calorimetry or DSC is used to observe the characteristic thermal accidents of a substance (dehydration, crystallisation, melting, etc.).

These analyses were performed on a METTLER-TOLEDO DSC unit. A known quantity of powder is placed in an aluminum cap in the "sample" crucible of the unit. A temperature gradient from 20 to 110° C. is produced at a rate of 5° C./min.

The melting point of ketoprofen is 94° C., the melting enthalpy thereof is equal to 116 J/g. The amorphisation is measured by comparing the melting peak of the active substance in the powder after treatment with "supercritical $CO_2$" according to the present invention to that of the corresponding physical mixture.

If the melting peak of ketoprofen disappears completely, then the amorphisation is considered to be equal to 100%.

Table 1 below shows the amorphisation % of the active substance after impregnation in the polymeric pharmaceutical excipient according to the invention (example 1a, 1b and 1c) or in lactose (example 1d) at T0 (immediately after the method according to the invention) or after storage for 2 months, 4 months, 7 months or 1 year.

TABLE 1

| Amorphisation | T0 | T0 + 2 months | T0 + 4 months | T0 + 7 months | T0 + 1 year |
|---|---|---|---|---|---|
| Example 1a | 100% | 100% | 100% | 100% | 100% |
| Example 1b B | 100% | 100% | 100% | 100% | |
| Example 1c | 100% | 100% | 100% | 100% | |
| Example 1d | 0% | | | | |

The samples were stored without any special precautions. The DSC analysis was carried out a number of time over one year and demonstrates that the amorphisation of the active substance is stabilised in the case of examples 1a, 1b and 1c.

After the DSC analysis, it is observed that the amorphisation rate of ketoprofen is zero in the case of example 1d.

The use of lactose as a carrier does not result in a stabilised solid dispersion. Similarly, for all the tests conducted with a cyclodextrin in the various examples in the patent WO2004/096284: the absence of water added during step b) of the method according to the present invention prevents complexing; therefore, no amorphisation takes place.

Lactose (two glucose units) and cyclodextrin (seven glucose units) are oligosaccharides and not polymers.

Acceleration of Dissolution Kinetics with Example 1a, 1b and 1c (Super-Disintegrating Agent)
Analytical Protocol:

In a 100 ml Erlenmeyer, introduce an accurately measured test sample equivalent to 50 mg of ketoprofen, pure or impregnating the cross-linked PVP. Add 50 ml of water. Place under magnetic stirring at 400 rpm in a water bath at 37° C.+/−2° C. Take a 2 ml sample under magnetic stirring at 5, 15 and 30 minutes. Filter these samples on Gelman GHP Acrodisc 0.45 μm polypropylene filters. The solution should be clear.

Determine the ketoprofen content by means of liquid chromatography.

The results are compiled in table 2 below:

TABLE 2

| | CARRIER | Ketoprofen % assay | Dissolution (μg/ml) | | |
|---|---|---|---|---|---|
| | | | 15 min | 30 min | 60 min |
| ketoprofen | / | / | 173 | 179 | 171 |
| Physical mixture | Cross-linked PVP XL10 | 29.3 | 157 | 177 | 172 |
| Example 1a | Cross-linked PVP XL10 | 29.3 | 279 | 310 | 311 |
| Example 1b | Metolose SM 4 | 31.21 | 399 | 437 | 459 |
| Example 1c | Benecel HPMC | 31.65 | 399 | 495 | 556 |
| Example 1d | Lactose | 30.13 | 104 | 176 | 183 |

The method according to the present invention makes it possible to enhance the dissolution kinetics of ketoprofen.

Example 2

With Vinflunine

2a: Vinflunine Base/Carboxymethyl Cellulose

Powder mixture: 1 g of Vinflunine base in crystalline form+2 g of Sodium Croscarmellose manually with a mortar (step a) of the method according to the present invention).

Treatment with SC $CO_2$ at 150 bar, 50° C., 2 hrs (step b) of the method according to the present invention) by pressurising a controlled-temperature high-pressure autoclave containing the mixture.

Recovery of the powder (step c) of the method according to the present invention) by depressurising the autoclave.

Acceleration of Dissolution Kinetics with Example 2a (Super-Disintegrating Agent)
Analytical Protocol:

In a 100 ml Erlenmeyer, introduce an accurately measured test sample equivalent to 50 mg of vinflunine. Add 50 ml of pH 6.8 buffer. Place under magnetic stirring at 400 rpm. Take a 2 ml sample under magnetic stirring at 15, 30, 60 and 120 minutes. Filter these samples on Gelman GHP Acrodisc 0.45 μm polypropylene filters. The solution should be clear.

Determine the vinflunine content by means of liquid chromatography.

The results are compiled in table 3 below:

TABLE 3

| | CARRIER | Vinflunine % assay | Dissolution (μg/ml) | | | |
|---|---|---|---|---|---|---|
| | | | 15 min | 30 min | 60 min | 120 min |
| Vinflunine base | / | / | 252 | 387 | 520 | 606 |
| Physical mixture | Sodium croscarmellose | 28.9 | 274 | 372 | 416 | 636 |
| Example 2a | Sodium croscarmellose | 28.9 | 765 | 801 | 854 | 807 |

The method according to the present invention makes it possible to enhance the dissolution kinetics of vinflunine base.

Increase in Bioavailability with Example 2a
Analytical Protocol:

The study was conducted with exploratory Pk on rats: 2 mg/kg in a single dose, oral route Administration vehicle: distilled water (Aguettant)
Fasted rats
Positive more Electrospray (ESI+) detection LC/MS/MS (liquid chromatography/mass spectrometry/mass spectrometry) bioanalysis method
Pharmacokinetic analysis with Kinetica (Thermo Instruments, US)

The results are compiled in table 4 below:

TABLE 4

| Time (min) | Vinflunine base | Example 2a |
|---|---|---|
| 0 | 0 | 0 |
| 0.25 | 19.37 | 39.13 |
| 0.5 | 11.75 | 32.30 |
| 1 | 17.90 | 28.07 |
| 2 | 14.93 | 27.23 |
| 4 | 13.80 | 28.70 |
| 6 | 12.03 | 19.93 |
| 8 | 10.88 | 18.27 |
| 24 | 2.59 | 3.39 |
| Pharmacokinetic parameters | | |
| Cmax (ng/ml) | 19.37 | 39.13 |
| Tmax (h) | 0.25 | 0.25 |
| AUClast (ng · h/ml) | 199.80 | 340.10 |
| Half-life (h) | 7.90 | 6.90 |
| CL (L/h) | 8.70 | 5.40 |

The method according to the present invention makes it possible to enhance the oral bioavailability of vinflunine base (increase in AUC and Cmax).

Example 3

With Milnacipran

3a Milnacipran/Methyl Cellulose

Powder mixture: 1.5 g of Milnacipran hydrochloride (PFM) in crystalline form+7.5 g of Metolose SM4 (Seppic) manually with a mortar (step a) of the method according to the present invention).

Treatment with SC $CO_2$ at 150 bar, 80° C., 2 hrs (step b) of the method according to the present invention) by pressurising a controlled-temperature high-pressure autoclave containing the mixture.

Recovery of the powder (step c) of the method according to the present invention) by depressurising the autoclave.

3b Milnacipran/HPMC

Powder mixture: 1.5 g of Milnacipran hydrochloride (PFM) in crystalline form+7.5 g of HPMC (Benecel) manually with a mortar (step a) of the method according to the present invention).

Treatment with SC $CO_2$ at 150 bar, 80° C., 2 hrs (step b) of the method according to the present invention) by pressurising a controlled-temperature high-pressure autoclave containing the mixture.

Recovery of the powder (step c) of the method according to the present invention) by depressurising the autoclave.

Delay Effect—Delayed Release (Controlled Release System), with Example 3a and 3b Analytical Protocol:

In a 100 ml Erlenmeyer, introduce an accurately measured test sample equivalent to 100 mg of milnacipran. Add 50 ml of water. Place under magnetic stirring at 400 rpm. Take a 2 ml sample under magnetic stirring at 1, 5, 15, 30 and 60 minutes. Filter these samples on Gelman GHP Acrodisc 0.45 μm polypropylene filters. The solution should be clear. Make a 1:5 dilution in mobile phase.

Determine the milnacipran content by means of liquid chromatography.

The results are compiled in table 5 below:

TABLE 5

| | Milnacipran | | Dissolution (g/l) | | | | |
|---|---|---|---|---|---|---|---|
| | CARRIER | % assay | 1 min | 5 min | 15 min | 30 min | 60 min |
| Milnacipran hydrochloride | / | / | 10 | 10.1 | 10.1 | 10.1 | 10.2 |
| Example 3a | methyl cellulose | 16.8 | 3.2 | 4.0 | 5.4 | 6.7 | 8.2 |
| Example 3b | HPMC | 14.9 | 0.3 | 0.6 | 0.9 | 1.2 | 1.7 |

The method according to the invention enables the delayed release of Milnacipran Hydrochloride (a completely soluble active substance).

Comparative Example 4

This example was performed according to the protocol in the patent application WO 99/25322. In this document, the extraction step for obtaining "saturated $CO_2$" is the limiting step, since the active substances are frequently considered to be insoluble in supercritical $CO_2$.

Milnacipran/hydroxypropyl methyl cellulose (HPMC) extraction/percolation 40 grams of Milnacipran is placed in an extraction cell, 8 grams of Benecel MP 843 (hydroxypropyl methyl cellulose) is placed in a column downstream from the cell. A flow of 5 kg/hr of SC $CO_2$ at 150 bar and 70° C. is applied for 3 hours.

The powder recovered in the column is analysed by means of HPLC: no trace of Milnacipran is detected. The insoluble active substance was not extracted and thus was not percolated through HPMC.

The invention claimed is:

1. Batch method for impregnating a polymeric pharmaceutical carrier with an active substance, wherein it comprises the following consecutive steps:
   a) mixing the active substance and the non-porous polymeric pharmaceutical carrier chosen from disintegrating agents, filler agents, or mixtures thereof, the pharmaceutical carrier being in solid form and insoluble in supercritical $CO_2$ and not being non-cross-linked polyvinylpyrrolidone;
   b) performing a molecular diffusion step in the absence of water by contacting, in static mode without stirring, the mixture obtained in step a) with supercritical $CO_2$ at a pressure between 80 and 170 bar and at a temperature between 31 and 90° C. for between 1 and 6 hours,
   c) recovering the polymeric pharmaceutical carrier impregnated with the active substance obtained in step b), the impregnated pharmaceutical carrier being non-porous and being in solid form and the active substance being in amorphous form,
   and in that the method is implemented in the absence of an additional solvent.

2. The method according to claim 1, wherein the polymeric pharmaceutical carrier is selected from the group consisting of cross-linked polyvinylpyrrolidone, carboxymethyl cellulose, hydroxypropyl methyl cellulose, methyl cellulose and mixtures thereof.

3. The method according to claim 1, wherein the mass ratio between the active substance and the polymeric pharmaceutical carrier in the impregnated polymeric pharmaceutical carrier is between 1 and 60%.

4. The method according to claim 1, wherein the active substance is selected from the group consisting of ketoprofen, vinflunine, milnacipran, fenofibrate, iron sulphate monohydrate and iron sulphate heptahydrate.

5. The method according to claim 1, wherein the temperature in step b) is between 40 and 85° C.

6. The method according to claim 1, wherein the pressure in step b) is between 100 and 160 bar.

7. The method according to claim 1, wherein the contact time in step b) is between 1 and 3 hours.

8. The method according to claim 1, wherein the active substance during step a) is in powder form.

9. The method according to claim 3, wherein the mass ratio between the active substance and the polymeric pharmaceutical carrier in the impregnated polymeric pharmaceutical carrier is between 10 and 35%.

10. The method according to claim 5, wherein the temperature in step b) is between 50 and 80° C.

11. The method according to claim 6, wherein the pressure in step b) is equal to 150 bar.

12. The method according to claim 7, wherein the contact time in step b) is equal to two hours.

13. The method according to claim 8, wherein the active substance during step a) is in crystalline powder form.

* * * * *